US012653507B2

(12) United States Patent
Labyed et al.

(10) Patent No.: US 12,653,507 B2
(45) Date of Patent: Jun. 16, 2026

(54) ULTRASOUND-DERIVED PROXY FOR PHYSICAL QUANTITY

(71) Applicant: Siemens Medical Solutions USA, Inc., Malvern, PA (US)

(72) Inventors: Yassin Labyed, Carlsbad, CA (US); Andrzej Milkowski, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1017 days.

(21) Appl. No.: 16/949,643

(22) Filed: Nov. 9, 2020

(65) Prior Publication Data
US 2022/0142614 A1 May 12, 2022

(51) Int. Cl.
*A61B 8/00* (2006.01)
*G16H 30/40* (2018.01)

(52) U.S. Cl.
CPC ............ *A61B 8/5223* (2013.01); *A61B 8/465* (2013.01); *A61B 8/467* (2013.01); *A61B 8/485* (2013.01); *A61B 8/5261* (2013.01); *G16H 30/40* (2018.01); *A61B 8/587* (2013.01)

(58) Field of Classification Search
None
See application file for complete search history.

(56) References Cited

U.S. PATENT DOCUMENTS

2010/0305928 A1* 12/2010 Cohen .................... G09B 23/30
703/11
2013/0225994 A1 8/2013 Hsu et al.

2013/0262062 A1* 10/2013 Sudama .................. G06F 30/23
703/6
2013/0296743 A1 11/2013 Lee et al.
2016/0155236 A1 6/2016 Davey
2017/0296148 A1 10/2017 Niemiec et al.
2018/0100907 A1 4/2018 Soza et al.
(Continued)

FOREIGN PATENT DOCUMENTS

CN 103536315 1/2014
CN 104081486 10/2014
(Continued)

OTHER PUBLICATIONS

Han et al. (Assessment of Hepatic Steatosis in Nonalcoholic fatty liver disease by using quantitative US, Radiology, Feb. 2020) (Year: 2020).*

(Continued)

*Primary Examiner* — Michael J Carey
*Assistant Examiner* — Marjan Saboktakin

(57) ABSTRACT

For ultrasound-based proxy estimation with an ultrasound scanner, one or more ultrasound measurements are converted to a biomarker of a different modality, such as providing a measurement of a standard biomarker from histology or a lab test assay. The conversion uses a user-selected model, allowing for selection of one of various models relating ultrasound measurements to the biomarker. The ultrasound scan sequence may be optimized to the one or more biomarkers and the user-selected model. This improvement in use of ultrasound measurements relative to standard biomarkers may more likely result in acceptance of the less costly and more easily obtained ultrasound measures in diagnosis.

19 Claims, 3 Drawing Sheets

30 User Selection of Conversion Model

32 Scan in Sequence Optimized to Model

33 Estimate Ultrasound Quantities

34 Convert from Ultrasound Quantities to Non-Ultrasound Biomarker

36 Machine-Learnt Classifier Model

37 Linear Model

38 Display Value for Non-Ultrasound Biomarker

(56) References Cited

U.S. PATENT DOCUMENTS

| | | | |
|---|---|---|---|
| 2018/0228463 A1 | 8/2018 | Shamdasani et al. | |
| 2018/0289323 A1* | 10/2018 | Labyed .................. | A61B 8/463 |
| 2020/0205786 A1 | 7/2020 | Labyed | |
| 2020/0237347 A1 | 7/2020 | De Beni et al. | |

FOREIGN PATENT DOCUMENTS

| | | | |
|---|---|---|---|
| CN | 105474219 | 4/2016 | |
| CN | 106137249 | 11/2016 | |
| CN | 108537794 | 9/2018 | |
| CN | 109567861 | 4/2019 | |
| CN | 111281425 | 6/2020 | |
| CN | 111492437 | 8/2020 | |
| JP | 2012095691 | 5/2012 | |
| JP | 5710341 | 4/2015 | |
| JP | 2020503142 | 1/2020 | |
| KR | 100438903 | 7/2004 | |
| KR | 1020180014773 | 2/2018 | |
| KR | 20190080121 | 7/2019 | |
| KR | 102258776 | 5/2021 | |
| KR | 1020210116268 | 9/2021 | |
| KR | 1020220101688 | 7/2022 | |
| WO | WO-2020044477 A1 * | 3/2020 ............. | A61B 8/463 |

OTHER PUBLICATIONS

Ballestri, Stefano, et al. "Ultrasonographic fatty liver indicator detects mild steatosis and correlates with metabolic/histological parameters in various liver diseases." Metabolism 72 (2017): 57-65.

D'hooge, Jan, et al. "Nonlinear propagation effects on broadband attenuation measurements and its implications for ultrasonic tissue characterization." The Journal of the Acoustical Society of America 106.2 (1999): 1126-1133.

Fahey, Brian J., et al. "Acoustic radiation force impulse imaging of the abdomen: demonstration of feasibility and utility." Ultrasound in medicine & biology 31.9 (2005): 1185-1198.

Han, Aiguo, and William D. O'Brien. "Structure function estimated from histological tissue sections." IEEE transactions on ultrasonics, ferroelectrics, and frequency control 63.9 (2016): 1296-1305.

Siddappa, Jagdeesh K., et al. "Correlation of ultrasonographic parameters with serum creatinine in chronic kidney disease." Journal of clinical imaging science 3 (2013). pp. 1-6.

Vermehren, Johannes, et al. "Comparison of acoustic radiation force impulse imaging with transient elastography for the detection of complications in patients with cirrhosis." Liver International 32.5 (2012): 852-858.

Yang, Kuen Cheh, et al. "Ultrasound imaging in nonalcoholic liver disease: current applications and future developments." Quantitative imaging in medicine and surgery 9.4 (2019): 546-551.

Yassin Labyed et al; "Novel Method for Ultrasound-Derived Fat Fraction Using an Integrated Phantom"; Journal of Ultrasound in Medicine; Jun. 11, 2020.

Michael Baumann et al; "Prostate biopsy tracking with deformation estimation"; Medical image analysis; May 2, 2012.

Mark. P. Wylie et al; "Soft tissue cutting with ultrasonic mechanical waveguides"; International congress on ultrasonics; Sep. 19, 2012.

* cited by examiner

30 — User Selection of Conversion Model

32 — Scan in Sequence Optimized to Model

33 — Estimate Ultrasound Quantities

34 — Convert from Ultrasound Quantities to Non-Ultrasound Biomarker

36 — Machine-Learnt Classifier Model

37 — Linear Model

38 — Display Value for Non-Ultrasound Biomarker

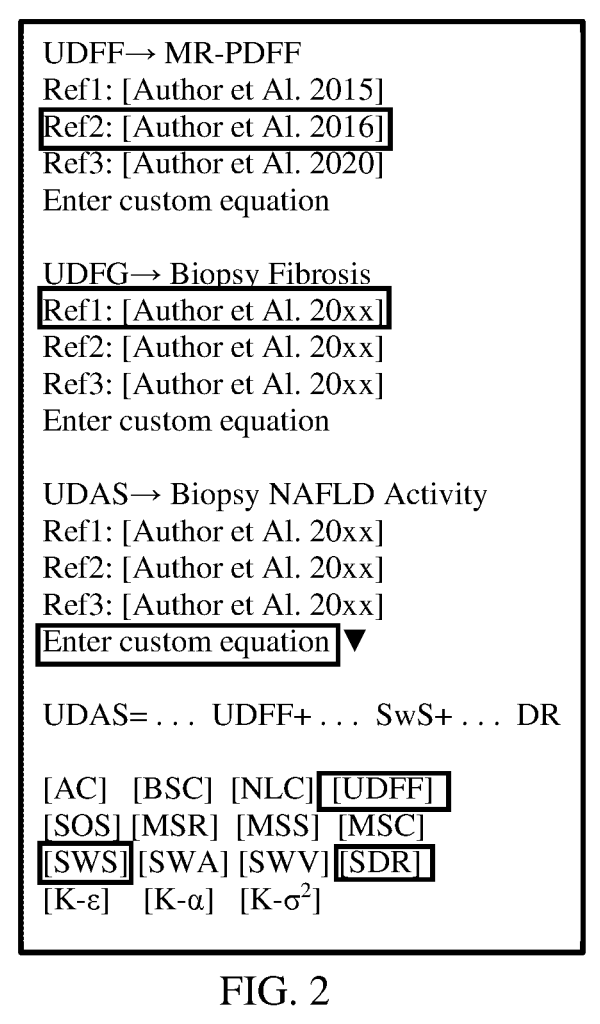

UDFF→ MR-PDFF
Ref1: [Author et Al. 2015]
Ref2: [Author et Al. 2016]
Ref3: [Author et Al. 2020]
Enter custom equation UDFG→ Biopsy Fibrosis
Ref1: [Author et Al. 20xx]
Ref2: [Author et Al. 20xx]
Ref3: [Author et Al. 20xx]
Enter custom equation UDAS→ Biopsy NAFLD Activity
Ref1: [Author et Al. 20xx]
Ref2: [Author et Al. 20xx]
Ref3: [Author et Al. 20xx]
Enter custom equation ▼

UDAS= . . . UDFF+ . . . SwS+ . . . DR

[AC]  [BSC]  [NLC] [UDFF]
[SOS] [MSR]  [MSS]  [MSC]
[SWS] [SWA]  [SWV] [SDR]
[K-ε]  [K-α]  [K-$\sigma^2$]

FIG. 2

ULTRASOUND-DERIVED PROXY FOR PHYSICAL QUANTITY

BACKGROUND

The present embodiments relate to ultrasound imaging. Ultrasound imaging may be used to measure tissue characteristics, but these characteristics may be different than standards commonly used in the medical community. A measurement for one modality may become standard, such as a histology-based score being a standard. Various modalities provide different measurements. Biomarkers from different modalities often measure different physical properties with different units and/or scales. The measurements from different modalities may be confusing where the units and/or scales are different than for the standard. Clinicians may consider quantitative ranges of the ultrasound-based biomarkers as proxies for corresponding ranges of quantities derived from histological analysis or another standard, but this conversion may be inexact or not relied upon. This may result in slow adoption and difficult interpretation of a newly developed ultrasound biomarker.

SUMMARY

By way of introduction, the preferred embodiments described below include methods, instructions, and systems for ultrasound-based proxy estimation with an ultrasound scanner. One or more ultrasound measurements are converted to a biomarker of a different modality, such as providing a measurement of a standard biomarker from histology or a lab test assay. The conversion uses a user-selected model, allowing for selection of one of various models relating ultrasound measurements to the biomarker. The ultrasound scan sequence may be optimized to the one or more biomarkers and the user-selected model. This improvement in use of ultrasound measurements relative to standard biomarkers may more likely result in acceptance of the less costly and more easily obtained ultrasound measures in diagnosis.

In a first aspect, a method is provided for an ultrasound-based proxy estimation with an ultrasound scanner. A user selection of a first conversion model for converting from one or more ultrasound measurements to a biomarker of another modality than ultrasound is received. The ultrasound scanner scans a patient with a sequence of ultrasound transmissions. The ultrasound scanner estimates one or more quantitative ultrasound values for the one or more ultrasound measurements from ultrasound data resulting from the scanning. The one or more quantitative ultrasound values are converted by the first conversion model to a value for the biomarker of the other modality than ultrasound. A value for the biomarker for the patient is displayed.

In a second aspect, a method is provided for an ultrasound-based proxy estimation with an ultrasound scanner. A user selection of a first conversion model for converting from first and second ultrasound measurements to a biomarker of another modality than ultrasound is received. The ultrasound scanner scans a patient with a sequence of ultrasound transmissions. The sequence is defined based on the first conversion model. The ultrasound scanner estimates first and second quantitative ultrasound values for the first and second ultrasound measurements from ultrasound data resulting from the scanning. The first and second quantitative ultrasound values are converted by the first conversion model to a value for the biomarker of the other modality than ultrasound. The value for the biomarker has a different scale and/or unit than the first and second quantitative ultrasound values. A value for the biomarker for the patient is displayed.

In a third aspect, a system is provided for an ultrasound-based proxy estimation. A user input is configured to receive user entry of a first model relating ultrasound parameters to a non-ultrasound parameter. The first model is in a list of multiple models for the non-ultrasound parameter. A beamformer is configured to transmit and receive sequences of pulses in a patient with a transducer. The sequence of pulses being for the ultrasound parameters and optimized based on the model. An image processor is configured to generate a value for the non-ultrasound parameter from values of the ultrasound parameters. The values of the ultrasound parameters are estimated using the transmit and receive sequences of the pulses. A display is configured to display the score for the index of the disease activity.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 2 illustrates example model selection for different standard biomarkers;

DETAILED DESCRIPTION OF THE DRAWINGS AND PRESENTLY PREFERRED EMBODIMENTS

Figure 1:
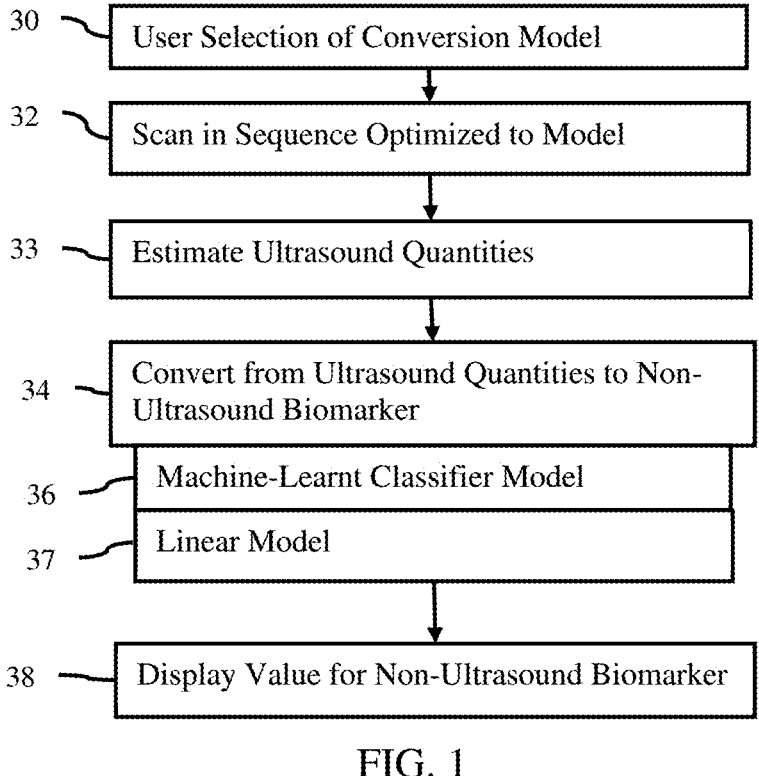
FIG. 1 is a flow chart diagram of one embodiment of a method for an ultrasound-based proxy estimation with an ultrasound scanner.

Measurement values of ultrasound-derived parameters are mapped to new values serving as proxies to established biomarkers from another modality. For example, a disease-related activity in tissue, such as liver, is measured using ultrasound. Nonalcoholic fatty liver disease (NAFLD) is characterized by excess hepatic fat accumulation as well as hepatic fibrosis. Fat fraction may be measured as an indicator of NAFLD. Fat fraction in the liver or other tissues, such as breast tissue, and/or other tissue properties (e.g., degree of fibrosis) provide diagnostically useful information. Magnetic resonance imaging (MRI) may measure the proton density fat fraction (PDFF) as a biomarker of hepatic fat content. MRI may be used to further estimate NAFLD activity score (NAS). However, MRI is not widely available and is expensive. Ultrasound may be used to determine the fat fraction by measuring other characteristics of tissue.

Over 25% of patients with NAFLD develop non-alcoholic steatohepatitis (NASH). NASH may progress to cirrhosis and hepatocellular carcinoma. NAS is used to diagnose and monitor changes or level of NASH. NAS is provided from histologic evaluation of liver biopsies and is calculated as an unweighted sum of the observed steatosis, lobular inflammation, and ballooning scores. Ultrasound measures showing fat fraction do not directly map to NAS. A score of an index is estimated using ultrasound, allowing for rapid, inexpensive, and non-invasive estimation of the disease activity. An ultrasound-derived NAS is estimated, avoiding biopsy or MRI.

Quantitative ultrasound (QUS) is used for screening, diagnosing, monitoring, and/or predicting health conditions. The complexity of human tissue may be measured using multiple QUS parameters for accurate characterization of that tissue. For example, liver fat fraction is estimated using a multi-parametric approach that combines quantitative parameters extracted from the received signals of different wave phenomena, such as scattering and attenuation of longitudinal waves, propagation and attenuation of shear waves, and/or propagation and attenuation of on-axis waves from acoustic radiation force impulse (ARFI). As another example, NAS is predicted using quantitative ultrasound. NAS is predicted based on ultrasound estimates of tissue mechanical and acoustic properties. A model of at least three properties of the liver including the acoustic backscatter coefficient, the shear wave velocity, and the shear wave damping ratio is used to predict NAS. Histological NAS is the sum of steatosis, lobular inflammation, and ballooning histologic scores but requires biopsy. The ultrasound-derived model pairs appropriate mechanical and acoustic properties with NAS features. The ultrasound-derived fat fraction, such as based on backscatter, attenuation, and/or sound speed, is used as a measure of steatosis grade. Shear wave damping ratio is used as a measure of inflammation, and shear wave speed is used as a measure of ballooning. Other ultrasound measurements may be used. Other models relating ultrasound quantitative measures to fat fraction, NAS, or other biomarkers may be used.

The ultrasound-derived measurements for any of the models are proxies for physical quantities measured by other modalities. To facilitate the interpretation and adoption of newly developed ultrasound biomarkers, it is important to represent the measurements as predictors (e.g., similar units and scales) of currently established biomarkers from other modalities (imaging, lab test assays, histology-based scores, magnetic resonance (MR), computer tomography (CT), etc.). Using model-based conversion, newly developed ultrasound-derived biomarkers are represented in units and scales that are intuitive and/or similar to those from established biomarkers from other modalities. This facilitates the interpretation of the values and speeds up the adoption of the new ultrasound technology.

Although biopsy is considered the gold standard for determining the characteristics of many diseases, it is not feasible as a reference standard in studies of the general population. Noninvasive imaging and laboratory assay biomarkers have been developed as surrogates for histologic features. In many cases, a disease process can be characterized using one of many established biomarkers from different modalities. As an example, fibrosis can be assessed using ultrasound, MR, or blood serum test. Since ultrasound imaging may be more easily, quickly, and cheaply performed, ultrasound-derived parameters are mapped to values serving as proxies to established and clinically accepted biomarkers from other modalities.

Over time, different models or studies may relate the same or different measurements in different ways to the standard. In one embodiment, the predictors or proxies for non-ultrasound biomarkers are based on user-selected models employing quantitative ultrasound (QUS) measurements. QUS measurements include acoustic and mechanical properties derived from backscatter, shear wave, and speckle statistics data. To allow for versatility in proxy-type QUS measurements, custom and/or user-selected models based on reference publications are available to the user. Based on the selected model and/or the combination of models for different proxies (e.g., one for fat fraction and another for NAS), an optimized sequence is used to measure the QUS parameters as needed for the different models.

FIG. 1 shows one embodiment of a method for ultrasound-based proxy estimation with an ultrasound scanner. Ultrasound, through the use of one or different sequences and models, predicts common measures used today for diagnosis. Multiple QUS measurements, through a sequence of ultrasound transmissions, may improve prediction. A higher-order model or different models may improve prediction. The user selects the model or models to be used. A combination of models and/or sequences may allow ultrasound to estimate multiple biomarkers for other modes (e.g., histology or MR). With a single button press, a specialized sequence collects and processes the ultrasound data to produce a proxy or proxies for a non-ultrasound biomarker or biomarkers, such as a biomarker currently established as reference standards for assessing these pathologies. For example, the liver can suffer from a number of concurrent pathologies-steatosis, inflammation, fibrosis, iron overload, etc., each at a different stage of disease progression. The proxy estimation acts as an ultrasound liver lab test for assessing one or more conditions, similar to a serum lab test.

Figure 4:
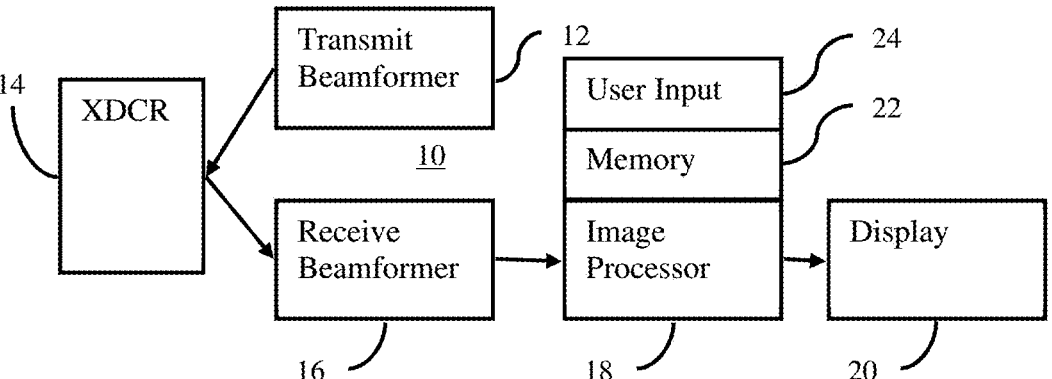
FIG. 4 is a block diagram of one embodiment of a system for an ultrasound-based proxy estimation.

The method is implemented by the system of FIG. 4 or a different system. A user selects a model to be used for a desired standard biometric (e.g., non-ultrasound biometric). A medical diagnostic ultrasound scanner performs the QUS measurements for the selected model by acoustically generating the waves and measuring the responses. An image processor of the scanner, computer, server, or other device estimates a value for the biomarker from the measurements using the model. A display device, network, or memory is used to output the value for the biomarker, providing an ultrasound proxy for the non-ultrasound standard based on the user selected model.

Additional, different, or fewer acts may be provided. For example, acts 30 and/or 38 are not provided. As another example, acts 36 and 37 are alternatives or may be used together, such as averaging results from both. In another example, acts for configuring the ultrasound scanner are provided. The acts are performed in the order described or shown (e.g., top to bottom or numerically), but may be performed in other orders.

In act 30, a user selects a conversion model or models. The ultrasound scanner or controller receives a user selection of the model or models for converting from one or more ultrasound measurements to a biomarker of another modality than ultrasound. The user selects from a list, or entry of an identifier is received by data transfer, memory location indication, and/or from a user input device.

The selection is from a list. For example, FIG. 2 shows three different publications or references and a custom field for each of three non-ultrasound biomarkers. In this example, the user selects to use the MR-PDFF, biopsy fibrosis, and NAS (Biopsy-based NAFLD Activity Score) biomarkers for a liver study. The biomarkers may be selected based on the imaging application (e.g., configuring the ultrasound scanner for liver imaging). For each non-ultrasound biomarker, the user selects one of the available options (e.g., one of the four options in FIG. 2). As new models are created, such as models more accurate for particular populations, the models are added to the lists for selection by the user. In alternative embodiments, the user navigates through a sequence of questions resulting from answers input by the user. In response, a most appropriate model for a given patient is selected.

The models may be proprietary, such as based on work by an ultrasound manufacturer or a study performed for a hospital. The models may be public, such as from published studies or articles. The list of models may include reference information for the corresponding study. The models may be custom, such as the user altering an existing model or providing their own model. The model may be customized for a given medical facility or institution (e.g., for a hospital system). Rather than being based only on a study or published reference, an altered or original model for a restricted group (e.g., a given physician or practice) is created. If there are new or improved models, the models are provided for selection. If models for different patient populations become available, the models are provided for selection.

The custom model may have been previously created. The user inputs an identification of the previously customized model. The custom model may be created as needed or used. The user interface may list options of different QUS measurements and allow definition of the function to provide the biomarker from the QUS measurements. A user may want to specify a custom formula that uses a number of acoustic parameters as inputs. The system will automatically fire an optimal sequence to estimate those parameters and use them in the custom equation. This option could facilitate improving the models in the field as clinicians collect more data and have a way to compare models on the fly. For the custom model, the selection is based on a model not provided by a manufacturer of the ultrasound system. For example, the manufacturer provides models based on publications or studies but also allows the user to identify other custom models for selection.

The selection may be nested, such as the user selecting the lab tests or biomarkers of interest. The user selects the lab tests (e.g., fat content, inflammation, etc.). For each biomarker, one or more models are provided as options. The user selects the models (e.g., based on reference publication) for those tests. For example, different studies may relate different ultrasound information to a biomarker. The user can select which study and corresponding model to use for converting from one or more (e.g., two) ultrasound measurements to a biomarker of a standard, such as histology or MR-based standard biomarker (measurement). The system sets up a sequence based on user selection. The data is processed and presented to the user accordingly, providing efficient quantitative usability in ultrasound-based proxy of non-ultrasound biomarkers. Alternatively, the ultrasound scanner is configured for a given biomarker and the user only selects the model for that one biomarker.

For each model, one or more ultrasound measurements are defined. Each model provides a list of different ultrasound QUS measurements to be performed in order to convert or estimate the value for the non-ultrasound biomarker. The model also defines the conversion or relationship of values of the ultrasound QUS measurements to the value of the non-ultrasound biomarker.

In act 32, the ultrasound scanner scans the patient. The scanning is for generating values of one or more QUS measures of tissue in the patient. The QUS measurements may be for scatter. The QUS measures may be for shear wave propagation. The QUS measures may be for an ARFI measure of axial displacement. The QUS measurements may be for acoustic properties, including attenuation coefficient (AC), backscatter coefficient (BSC), nonlinearity coefficient (NLC), ultrasound derived fat fraction (UDFF), speed of sound (SOS), mean scatterer radius (MSR), mean scatterer spacing (MSS), mean scatterer concentration (MSC), shear wave speed (SWS), shear wave attenuation (SWA), shear damping ratio (SDR), and/or homodyned K distribution parameters [K–$\varepsilon,\alpha,\sigma$].

The measure or measures of scatter measure a tissue response to a longitudinal wave transmitted from an ultrasound scanner. The scattering or echo of the longitudinal wave impinging on the tissue is measured. Any measure of scatter may be used. Acoustic properties like the AC, BSC, MSR, MSS, and MSC are estimated from B-mode-like frames by analyzing the frequency and depth dependence of the returned ultrasound signals. Example scatter parameters include sound speed, sound dispersion, angular scattering coefficient (e.g., backscatter coefficient), frequency-dependent attenuation coefficient, attenuation coefficient slope, spectral slope of the normalized log-spectrum, spectral intercept of the normalized log-spectrum, spectral midband of the normalized log-spectrum, effective scatterer diameter, acoustic concentration, scatterer number density, mean scatterer spacing, nonlinearity parameter (B/A), and/or ratio of coherent to incoherent scattering.

Analysis of channel data is typically used to obtain estimates of the SOS. Estimating the NLC requires a sequence of transmissions at different transmit powers and analyzing the change is AC or BSC with respect to transmit power. K-distribution parameters are obtained by analyzing speckle statistics of reconstructed US images.

Any shear wave parameter or parameters may be determined. Properties likes SWS, SWA, SDR, Young's modulus (SWE) and shear wave viscosity (SWV) are estimated by analyzing displacement profiles from tracking shear waves generated by ultrasound push pulses. For example, a shear wave speed or velocity in tissue is measured. Other shear wave parameters include angular and/or frequency-dependent shear wave speed, angular and frequency-dependent shear wave attenuation, angular and/or frequency-dependent storage modulus, angular and/or frequency-dependent loss modulus, viscosity, and/or angular and/or frequency-dependent acoustic absorption coefficient.

Any ARFI measure may be used. For example, the attenuation of the longitudinal wave of the ARFI pulse may be estimated from displacements tracked at locations spaced from the focal point of the ARFI. The measures may be at the focal point or other locations along the axial scan line.

Any combination of QUS measures may be used. More than one measure may be performed. For example, the ultrasound system determines values for two or more scattering parameters of the patient tissue. In one embodiment, the acoustic attenuation coefficient, backscatter coefficient, and/or spectral slope of a logarithm of the frequency-dependent backscatter coefficient are measured.

The QUS measures to be used are based on the selected model or models. The sequence of ultrasound transmissions and receptions for scanning the patient is defined based on the conversion model or models. The conversion models define the input information, and the ultrasound scanner scans the patient to generate estimates for the input measurements. The ultrasound scanner automatically sets up a sequence or sequences to estimate parameters needed for any selected model or models. The selection is used to configure the scanning. A user may want to specify a custom formula that uses a number of acoustic parameters as inputs. The ultrasound system automatically fires an optimal sequence to estimate those parameters for use in the custom equation.

To perform the QUS measurements, the ultrasound scanner scans the patient. Different measurements use different transmission pulses and reception or ultrasound sequences. A transmission and/or reception for one measurement may be used for other measurements. A sequence of transmit and receive events is performed to acquire the signals to estimate the quantitative ultrasound scatter, shear, and/or ARFI parameters. In one embodiment, a one, two, or three-dimensional region is scanned by a B-mode sequence (e.g., transmit a broadband (e.g., 1-2 cycle) transmit beam and form one or more responsive receive beams). Repetition with or without different transmit and/or receive settings may be used to measure the scatter once or to measure the scatter differently. In another embodiment, a pushing pulse or ARFI is transmitted to a focal location in the tissue. A reference scan for a resting state tissue position is performed before the pushing pulse or after the tissue returns to a resting state. The change in position or displacement of tissue at one or more locations spaced from the focal location are measured over time. Tracking scans are repetitively performed. Using correlation or other measure of similarity, the axial, 2D, or 3D shift of tissue from a reference time compared to a current tracking time is determined. The time of the maximum displacement indicates the time of a shear wave. The measurement of the shear wave parameters may be a function of frequency and/or angle. In yet another embodiment, the ARFI is transmitted along a scan line. Tracking scans are performed after transmission of the ARFI. The acoustic echoes from the tracking transmissions along the scan line are received. The received data is correlated with a reference from prior to or after ARFI-caused displacements. The amount of displacement as a function of time, location, transmit angle, and/or transmit frequency is determined. The amount of maximum displacement, displacement as a function of depth, and/or displacement as a function of time is used to calculate the ARFI measure.

Since the model or models define the one or more QUS measurements, a sequence of transmissions and receptions in the scan is initiated and performed in response to a single activation. The user is provided with tools to select or specify models to obtain one or multiple proxy measurements in a single button press. Rather than giving specific details of each sequence, the workflow allows model selection, which models define the scans to provide the sequence. The ultrasound scanner looks-up or uses rules to combine the transmissions and receptions for the QUS measurements. This optimal sequence based on user selection provides all proxy measurements with a single button press to activate scanning by the user. The ultrasound data for the single activation is gathered by scanning according to the sequence, ensuring that the measurements correspond to the same interrogated region. The single button press causes the ultrasound scanner to run the specialized sequence to collect and process all the necessary ultrasound data to produce proxies for non-ultrasound biomarkers. The specialized sequence consists of a number of acquisitions. The data from each acquisition is used to estimate one or more acoustic properties.

Where a model or models call for two or more QUS measurements, the measurements may be performed in any order. The sequence is created by sequential combination of the transmit and receptions to perform the QUS measurements. The sequence may be optimized. For example, the scans are interleaved. Interleaving the scans for different QUS measurements may speed up acquisition, reducing the time of the scanning for the sequence. Other optimizations are possible, such as adjusting transmit power, frequency, F #, or other transmit or receive characteristic based on feedback and/or the QUS measurements to be performed. Nonlinearity can cause a significant bias in attenuation and backscatter estimates, therefore transmit power optimization may be used for measuring attenuation while maintaining signal-to-noise ratio. The optimization may be performed based on thermal considerations. For example, ARFI is performed after transmissions for measurements not using ARFI. ARFI sequences many cause localized heating which could impact estimates of speed of sound and attenuation, so ARFI is performed later in an optimized sequence. The sequence is optimized in the sense that the sequence allows the user to obtain measurements in one scan from a combination of transmissions and receptions over shortest or short amount of time. The scans are ordered in the sequence in such a way that one scan doesn't impact estimates of another scan.

The sequence may be pre-determined. The possible combinations of QUS measurements, reflected by the possible combinations of one or more conversion models, are used to determine different sequences. Based on the user selection of the model or models, the corresponding optimized sequence is loaded. Alternatively, rules are provided. The hierarchy of rules is used to create the sequence. For example, a highest priority rule is to perform ARFI after other scans. Another rule is to interleave. Interleaving is performed where it does not violate the highest priority rule. The use of rules may allow for the user to define a custom model. The custom model has user-selected QUS measurements, so an optimized sequence for the user-selected QUS measurements is formed from the rules defining the sequence of the ultrasound transmissions for the measurements of the custom model.

The scanning of the sequence may be adaptive. The values of the QUS measurements and/or value of a non-ultrasound biomarker after conversion from the QUS measurements is used to adapt the scanning. The adaptation is another form of optimization of the sequence. In one example, initial scans are performed to get first estimates of ultrasound parameters. The estimates are then used to choose an optimized transmit/receive condition to improve accuracy and precision of the estimates. For example, the transmit frequency, bandwidth, transmit power, receive gain, etc. are adjusted in repetitions of the scanning. The adjustment is based on the first estimates, such as estimates of AC, BSC, and/or SOS. As another example, the sequence adapts based on the value for the biomarker in an iterative or adaptive calibration. Using a reference phantom method (RPM), a well characterized phantom is used to normalize system effects. The patient raw ultrasound data is processed and normalized iteratively through a number of reference phantoms. The value for the biomarker (e.g., the UDFF value) is used to adapt using the reference phantom with acoustic properties (AC, BSC) that are closest to those of the patient. The UDFF may indicate that the SOS used in estimating the AC and/or BCS is to be changed. The scan is repeated using the adapted SOS. In another example, there may be a mismatch of values, such as fat fraction showing normal while SOS shows fatty. The BCS used to determine fat fraction may be wrong due to this mismatch, so the scan is repeated with BCS relying on a new SOS.

Other adaptations of the sequence of scanning may be used. For example, for an estimate of the attenuation coefficient of the shear wave, the push pulse adapts. The center frequency, duration, f-number, or other characteristic of the push pulse is changed for a later transmission. The focus is tighter or weaker. The displacement to create the shear wave is larger or lesser. As another example, for an estimate of the absorption coefficient with an ARFI push pulse, another push pulse is transmitted with a tighter focus or longer duration. The change may improve signal-to-noise ratio (SNR) and/or reduce variability in the measurements.

In act 33, the ultrasound scanner estimates the value or values for the QUS measurement or measurements. The ultrasound data resulting from the scanning is used to estimate the value or values. The QUS values are estimated for the QUS measurements associated with the selected conversion model or models. For example, values for AC, BSC, SOS, and SWS are estimated for a model to predict NAS and/or FF. One or more of the values may use measurements responsive to ARFI.

A value or values for any of the various QUS measurements may be estimated. The data from the scanning is used to estimate one or more acoustic properties, such as AC, BSC, ESD, SD, SWS, SWV, NC, SOS, homodyned K-distribution parameters, or others. Acoustic properties like the AC, BSC, ESD, and SD are estimated from B-mode-like frames by analyzing the frequency and depth dependence of the returned ultrasound signals. Properties likes SWS and SWV are estimated by analyzing displacement profiles from tracking shear waves generated by ultrasound push pulses. Estimating the NC requires a sequence of transmissions at different transmit powers and analyzing the change in AC or BSC with respect to transmit power. Analysis of channel data is typically required to obtain estimates of the SOS. K-distribution parameters are obtained by analyzing speckle statistics of reconstructed US images. The values for these parameters are fed into conversion models for predicting the biomarkers.

In act 34, a processor converts the one or more QUS values to a value for the biomarker of the other modality than ultrasound. The conversion model or models convert the QUS values to the non-ultrasound biomarker, such as converting AC, BSC, and SWS to PDFF. Estimates are provided for the QUS measurements from the selected model or models. The models are used to convert the estimates to the biomarker or biomarkers, such as standard measurements from MR, CT, lab test assay, and/or histology.

For example, AC and BSC are converted to PDFF. As another example, SWE is converted to MRE. In yet another example, density is converted to HU. As yet another example, SWE is converted to FibroTest. As another example, AC and BSC are converted to proportion of cells with fat deposition. Other conversions may be used.

The biomarker has a different unity and/or scale than the QUS measurements. The conversion model converts to the units and/or scale of the established biomarker. For example, AC is given in dB/cmMHz and BSC is given in dB/cm-str, which units are converted to the % of fat fraction. As another example, SWE is given in kPa, which is converted to a fibrocity score in a 0-1 scale. The conversion may be from a linear or continuous scale to a different linear or continuous scale. The conversion may be from a linear or continuous scale to a non-linear or non-continuous scale, such as conversion to a score or ranking.

Other information may be used for estimating the value of the non-ultrasound biomarker. For example, clinical information for the patient is used. The clinical information may be the medical history, age, body-mass index, sex, fasting or not, blood pressure, diabetic or not, and/or a blood biomarker measure. Example blood biomarkers include alanine aminotransferase (ALT) level, aspartate aminotransferase (AST) level, and/or alkaline phosphatase (ALP) level. Any information about the patient may be input with the QUS estimates to determine the value of the biomarker.

Acts 36 and 37 represent two different embodiments for estimating in act 34. The different embodiments are alternatives. Other embodiments may be used. Both or multiple embodiments may be used, such as determining a value for a tissue property in two ways and then averaging the results or selecting the result most likely to be accurate.

In the embodiment of act 36, a machine-learnt classifier estimates the biomarker. The machine-trained classifier provides a nonlinear conversion model. Any machine learning and resulting machine-learnt classifier may be used. For example, a support vector machine, probabilistic boosting tree, Bayesian network, neural network, regression, or other machine learning is used.

The machine learning learns from training data. The training data includes various examples, such as tens, hundreds, or thousands of samples, and the ground truth. The examples include the input data to be used, such as values for scattering and shear wave propagation parameters. The ground truth is the value for the biomarker of each example. In one example, the machine learning is to learn to classify the fat fraction based on scattering and shear wave propagation parameters. The ground truth for the fat fraction is provided with a magnetic resonance (MR) scan providing proton density fat fraction (PDFF) or from histology. The MR-PDFF or histology provides a percentage of fat for a location or region. The percentage of fat is used as the ground truth so that the machine learning learns to classify the percentage of fat from input values for the ultrasound parameters. Other sources of ground truth may be used for a given tissue property, such as from modeling or other measurements.

In one embodiment, the machine learning trains a neural network. The neural network includes one or more convolution layers that learn a filter kernel to distinguish between the values of a biomarker. The machine training learns what weighted combination (e.g., convolution using learnt kernel) of input values indicates the output. The resulting machine-learnt classifier uses the input values to extract the distinguishing information and then classifies the biomarker based on the extracted information.

In the embodiment of act 37, a linear model is used instead of or in addition to a machine-learnt model. A predetermined or programmed function relates the input values to the output values. The function and/or weights used in the function may be determined experimentally. For example, the weights are obtained by a least square minimization.

Any linear function may be used. For example, the value of the biomarker is estimated from one or more scatter parameters and one or more shear wave propagation parameters. Any combination of addition, subtraction, multiplication, or division may be used. In one embodiment, two or more functions (e.g., weighted combinations of measures) are provided. One of the functions is selected based on the value of one of the parameters. A look-up table may be used to implement the function or as the function.

The conversion models for predicting the biomarkers are trained or created using clinical data, phantom data, and/or simulations. The conversion models may be regression models or machine learning classifiers. As an example, a proxy for MR-PDFF (steatosis) uses a polynomial fit of the AC, BSC, SOS, and NC. In another example, a proxy for histologic fibrosis grade is a logistic regression model using SWS. As another example, a proxy for histologic inflammation is a logistic regression model using AC, BSC, SOS, SWS, SWV and NC.

The conversion model represents a mapping, which is determined experimentally and/or theoretically. In an example, a conversion model is created to estimate MRI-PDFF from ultrasound. In an example approach, the conversion model is created by performing ultrasound scanning and liver biopsies on participants (e.g., human or animal participants). The conversion model is derived to predict triglyceride concentration based on ultrasound parameters. In another example, ultrasound and MRI proton density fat fraction (MRI-PDFF) are performed on participants. The model is derived to predict MRI-PDFF based on the ultrasound parameters. Existing models for predicting triglyceride concentration based on MRI-PDFF may be used to convert to the concentration. This would be useful since biopsies are increasingly less common. In yet another example approach, the conversion model is created based on simulations of ultrasound interaction with triglycerides in background tissue. The ultrasound backscatter coefficient is a function of triglyceride concentration, droplet size, and relative impedance to background material. These parameters are fed into trained models or look up tables for predicting the biomarkers.

Figure 3:
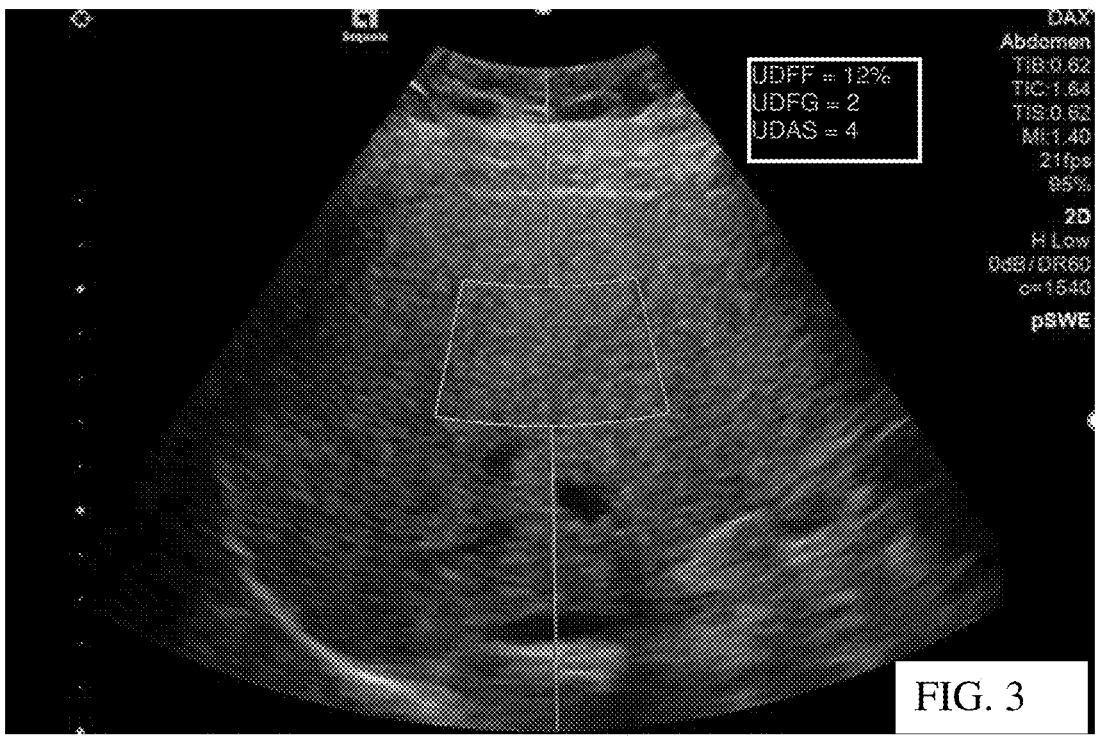
FIG. 3 is an example ultrasound image with values for non-ultrasound biomarkers.

In act 38, the ultrasound scanner, processor, or a display device displays the estimated biomarker or biomarkers for the patient. For example, an image of the fat fraction is generated. FIG. 3 shows an example ultrasound B-mode image with annotations for three biomarkers corresponding to three conversion models (i.e., UDFF=MRI-UDFF, UDFG=biopsy fibrosis score, and UDAS=NAS) selected by the user. A value representing the estimated biomarker is displayed on a screen. Alternatively or additionally, a graphic (e.g., curve or icon) representing the estimated biomarker is displayed. Reference to a scale or other reference may be displayed. In other embodiments, the value of the biomarker as a function of location is displayed by color, brightness, hue, luminance, or other modulation of display values in a one, two, or three-dimensional representation. The biomarker values may be mapped linearly or non-linearly to pixel color.

The value of the biomarker is indicated alone or with other information. For example, shear wave imaging is performed. The shear wave velocity, modulus or other information determined from tissue reaction to a shear wave is displayed. The displayed image represents shear wave information for the region of interest or the entire imaging region. For example, where shear velocity values are determined for all the grid points in a region of interest or field of view, the pixels of the display represent the shear wave velocities for that region. The display grid may be different from the scan grid and/or grid for which displacements are calculated.

The shear wave information is used for a color overlay or other modulation of display values. Color, brightness, luminance, hue, or other display characteristic is modulated as a function of the shear wave characteristic, such as the shear wave velocity. The image represents a two- or three-dimensional region of locations. The shear data is in a display format or may be scan converted into a display format. The shear data is color or gray scale data but may be data prior to mapping with gray scale or color scale. The information may be mapped linearly or non-linearly to the display values.

The image may include other data. For example, shear wave information is displayed over or with B-mode information. B-mode or other data representing tissue, fluid, or contrast agents in the same region may be included, such as displaying B-mode data for any locations with shear wave velocity below a threshold or with poor quality. The other data assists the user in determining the location of the shear information. In other embodiments, the shear wave characteristic is displayed as an image without other data. In yet other embodiments, the B-mode or other image information is provided without shear wave information.

The additional estimated value of the biomarker or values of the biomarkers are displayed substantially simultaneously with the shear wave, B-mode, color or flow mode, M-mode, contrast agent mode, and/or other imaging. Substantially accounts for visual perception of the viewer. Displaying two images sequentially with sufficient frequency may allow the viewer to perceive the images as being displayed at a same time. The component QUS measures used to estimate the biomarker may also be displayed, such as in a table.

Any format for substantially simultaneous display may be used. In one example, the shear wave or anatomy image is a two-dimensional image. The value of the biomarker is text (see FIG. 3), a graph, two-dimensional image, or other indicator of the values of the estimate. A cursor or other location selection may be positioned relative to the shear or anatomy image. The cursor indicates selection of a location. For example, the user selects a pixel associated with an interior region of a lesion, cyst, inclusion, or other structure. The biomarker for the selected location is then displayed as a value, a pointer along a scale, or other indication. In another example, the biomarker is indicated in a region of interest (sub-part of the field of view) or over the entire field of view.

FIG. 4 shows one embodiment of a system 10 for ultrasound-based proxy estimation. The system 10 implements the method of FIG. 1 or other methods. The system 10 includes a transmit beamformer 12, a transducer 14, a receive beamformer 16, an image processor 18, a display 20, a memory 22, and a user input 24. Additional, different or fewer components may be provided.

The system 10 is a medical diagnostic ultrasound imaging system. In alternative embodiments, the system 10 is a personal computer, workstation, PACS station, or other arrangement at a same location or distributed over a network for real-time or post acquisition imaging.

The user input 24 is a mouse, keyboard, trackball, touch pad, touch screen, buttons, sliders, knobs, and/or combinations thereof. Other user input devices may be used. The user input 24 is configured through hardware, software, and/or firmware to receive user entry of a model relating ultrasound parameters to a non-ultrasound parameter. The user interface of the system 10 uses the user input 24 for receiving entry of selection of one or more conversion models, such as selection from a list or selection by creating a custom model. For example, a conversion model for a biomarker or biomarkers of interest for a patient is selected from a list of available conversion models for that biomarker or biomarkers. The user input 24 is used to open the list and select from the list.

The transmit and receive beamformers 12, 16 form a beamformer used to transmit and receive using the transducer 14. A sequence of pulses are transmitted, and responses received based on operation or configuration of the beamformer. The beamformer scans for measuring scatter, shear wave, and/or ARFI parameters. The sequence is optimized based on the biomarkers (i.e., conversion models) selected using the user input 24. The beamformers 12, 16 are configured to transmit and receive sequences of pulses in a patient with the transducer 14 for the QUS parameters of the conversion model.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated electrical waveforms, one or more beams are formed. A sequence of transmit beams are generated to scan a two or three-dimensional region. Sector, Vector®, linear, or other scan formats may be used. The same region may be scanned multiple times using different scan line angles, F numbers, and/or waveform center frequencies. For flow or Doppler imaging and for shear imaging, a sequence of scans along the same line or lines is used. In Doppler imaging, the sequence may include multiple beams along a same scan line before scanning an adjacent scan line. For shear imaging, scan or frame interleaving may be used (i.e., scan the entire region before scanning again). Line or group of line interleaving may be used. In alternative embodiments, the transmit beamformer 12 generates a plane wave or diverging wave for more rapid scanning.

The same transmit beamformer 12 generates impulse excitations or electrical waveforms for generating acoustic energy to cause displacement. Electrical waveforms for acoustic radiation force impulses are generated. In alternative embodiments, a different transmit beamformer is provided for generating the impulse excitation. The transmit beamformer 12 causes the transducer 14 to generate pushing pulses or acoustic radiation force pulses.

The transducer 14 is an array for generating acoustic energy from electrical waveforms. For an array, relative delays focus the acoustic energy. A given transmit event corresponds to transmission of acoustic energy by different elements at a substantially same time given the delays. The transmit event may provide a pulse of ultrasound energy for displacing the tissue. The pulse may be an impulse excitation, tracking pulse, B-mode pulse, or pulse for other measures. Impulse excitation includes waveforms with many cycles (e.g., 500 cycles) but that occurs in a relatively short time to cause tissue displacement over a longer time. A tracking pulse may be B-mode transmission, such as using 1-5 cycles. The tracking pulses are used to scan a region of a patient.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer 14. The elements connect with channels of the transmit and receive beamformers 12, 16. Alternatively, a single element with a mechanical focus is used.

The receive beamformer 16 includes a plurality of channels with amplifiers, delays, and/or phase rotators, and one or more summers. Each channel connects with one or more transducer elements. The receive beamformer 16 is configured by hardware or software to apply relative delays, phases, and/or apodization to form one or more receive beams in response to each imaging or tracking transmission. Receive operation may not occur for echoes from the impulse excitation used to displace tissue. The receive beamformer 16 outputs data representing spatial locations using the receive signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or another band.

In coordination with the transmit beamformer 12, the receive beamformer 16 generates data representing the region. For tracking a shear wave or axial longitudinal wave, data representing the region at different times is generated. After the acoustic impulse excitation, the receive beamformer 16 generates beams representing locations along one or a plurality of lines at different times. By scanning the region of interest with ultrasound, data (e.g., beamformed samples) is generated. By repeating the scanning, ultrasound data representing the region at different times after the impulse excitation is acquired.

The receive beamformer 16 outputs beam summed data representing spatial locations. Data for a single location, locations along a line, locations for an area, or locations for a volume are output. Dynamic focusing may be provided. The data may be for different purposes. For example, different parts of a scan are performed for B-mode or tissue data than for displacement. Alternatively, the B-mode data is also used to determine displacement. As another example, data for different types of measures are acquired with a series of shared scans in the sequence optimized based on the selected conversion models, and B-mode or Doppler scanning is performed separately or using some of the same data.

The image processor 18 is a B-mode detector, Doppler detector, pulsed wave Doppler detector, correlation processor, Fourier transform processor, application specific integrated circuit, artificial intelligence processor, general processor, control processor, image processor, field programmable gate array, digital signal processor, analog circuit, digital circuit, combinations thereof or other now known or later developed device for detecting and processing information for display from beamformed ultrasound samples. In one embodiment, the image processor 18 includes one or more detectors and a separate image processor. The separate image processor is a control processor, general processor, digital signal processor, application specific integrated circuit, field programmable gate array, artificial intelligence processor, network, server, group of processors, combinations thereof or other now known or later developed device for calculating values of different types of parameters from beamformed and/or detected ultrasound data and/or for estimating a value for a biomarker from the values from the different types of ultrasound measures. For example, the separate image processor is configured by hardware, firmware, and/or software to perform acts 33-38 shown in FIG. 1.

The image processor 18 is configured to estimate a value for the non-ultrasound parameter from a combination of different types of ultrasound parameters. For example, a measured scatter parameter and one, two, or more measured shear wave parameters are used. The different types of ultrasound parameters are measured based on the transmit and receive sequence and calculation from the results. The values of the one or more measures of ultrasound parameters are determined for estimating a value of a non-ultrasound parameter, such as a histology, assay, MR, or CT parameter.

In one embodiment, the image processor 18 estimates the non-ultrasound parameter based on the different parameters or measures of tissue reaction to different types of wave fronts. The estimation applies a machine-learnt classifier. The input values of the measures with or without other information are used by a learnt matrix to output a value of the biomarker. In other embodiments, the image processor 18 uses a weighted combination of the values of the ultrasound parameters or a look-up table. For example, two or more functions are provided. Using the value of one or more parameters (e.g., shear wave speed), one of the functions is selected. The selected function uses the values of the same and/or different parameters to determine the value of the non-ultrasound parameter. A linear or non-linear mapping relates values of one or more ultrasound parameters to the value of the non-ultrasound parameter. For example, two or more scatter parameters are used to determine the value of the tissue property with a shear wave propagation selected function.

The processor 18 is configured to generate one or more images. For example, a shear wave velocity, B-mode, contrast agent, M-mode, flow or color mode, ARFI, and/or another type of image is generated. The shear wave velocity, flow, or ARFI image may be presented alone or as an overlay or region of interest within a B-mode image. The shear wave velocity, flow, or ARFI data modulates the color at locations in the region of interest. Where the shear wave velocity, flow, or ARFI data is below a threshold, B-mode information may be displayed without modulation by the shear wave velocity.

Other information is included in the image or displayed sequentially or substantially simultaneously. For example, a non-ultrasound estimate is displayed at a same time as the other image. A value or values of the biomarker map to display information. Where the non-ultrasound parameter is measured at different locations, the values may be generated as a color overlay in the region of interest in B-mode images. The shear wave velocity and biomarker may be combined as a single overlay on one B-mode image. Alternatively, the value or values of the non-ultrasound parameter is displayed as text or numerical value(s) adjacent or overlaid on a B-mode or shear wave imaging image (see FIG. 3).

The image processor 18 may be configured to generate other displays. For example, a shear wave velocity image is displayed next to a graph, text, or graphical indicators of the non-ultrasound parameter, such as fat fraction, degree of fibrosis, and/or disease activity.

The image processor 18 operates pursuant to instructions stored in the memory 22 or another memory for providing for user selection of a conversion model, optimization of the sequence for scanning based on the model, estimation from measures of tissue reaction, and/or estimation of the non-ultrasound parameter. The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a device, such as a CRT, LCD, projector, plasma, or other display for displaying one or two-dimensional images or three-dimensional representations. The two-dimensional images represent spatial distribution in an area. The three-dimensional representations are rendered from data representing spatial distribution in a volume. The display 20 displays an image representing the non-ultrasound parameter for a single location (e.g., averaged from estimates including adjacent locations), in a region of interest, or an entire image. For example, the display 20 displays a value for fat fraction and/or a score for an index of disease activity. The display of the tissue property and/or disease activity provides information for a standard, accepted or known biomarker for diagnosis.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for an ultrasound-based proxy estimation with an ultrasound scanner, the method comprising:

receiving a user selection of a first conversion model for converting from one or more ultrasound measurements to a non-ultrasound biomarker of another modality;

automatically defining a sequence of ultrasound transmissions that are configured to acquire the one or more ultrasound measurements required by the first conversion model;

scanning, by the ultrasound scanner, a patient with the sequence of ultrasound transmissions;

estimating, by the ultrasound scanner, one or more quantitative ultrasound values for the one or more ultrasound measurements from ultrasound data resulting from the scanning;

converting, by the first conversion model, the one or more quantitative ultrasound values to a value for the non-ultrasound biomarker of the other modality for the patient, wherein the non-ultrasound biomarker has a different unity and/or scale than the one or more quantitative ultrasound values; and displaying the value for the non-ultrasound biomarker for the patient.

2. The method of claim 1 wherein receiving the user selection comprises receiving the user selection from a displayed list of conversion models including the first conversion model, the displayed list of the conversion models including reference information for a study for the conversion model for each of the conversion models of the displayed list.

3. The method of claim 1 wherein receiving the user selection comprises receiving the user selection of the first conversion model as a custom model.

4. The method of claim 3 wherein receiving the user selection of the custom model comprises receiving an identification of a user-created model.

5. The method of claim 1 wherein estimating comprises estimating a plurality of the one or more quantitative ultrasound values for a plurality of the one or more ultrasound measurements, and wherein scanning with the sequence of ultrasound transmissions comprises scanning with the ultrasound transmissions for the plurality of the one or more ultrasound measurements being interleaved.

6. The method of claim 1 wherein estimating comprises estimating first and second values of the one or more quantitative ultrasound values for a first and second measurements of the one or more ultrasound measurements, the first measurement being in response to an acoustic radiation force impulse, and wherein scanning with the sequence of ultrasound transmissions comprises scanning with the ultrasound transmissions including the acoustic radiation force impulse, the acoustic radiation force impulse being performed after the ultrasound transmissions for the second measurement.

7. The method of claim 3, wherein scanning comprises scanning with the sequence of ultrasound transmissions, the sequence of ultrasound transmissions defined based on the custom model and a rule, the custom model defining the one or more measurements and the rule defining the sequence of the ultrasound transmissions for the one or more measurements of the custom model.

8. The method of claim 1 wherein scanning comprises scanning with the sequence of ultrasound transmissions being adaptive, the sequence of ultrasound transmissions comprising an initial scan that is performed to acquire a first estimate of ultrasound parameters, wherein the first estimate is used to define a subsequent scan of the sequence of ultrasound transmissions.

9. The method of claim 8 wherein scanning comprises scanning with the sequence of ultrasound transmissions being adaptive based on the value for the non-ultrasound biomarker.

10. The method of claim 1 wherein the first conversion model defines a plurality of the one or more ultrasound measurements, and wherein scanning comprises initiating and performing the scanning for the plurality of the one or more ultrasound measurements in response to a single activation.

11. The method of claim 1 wherein estimating the one or more ultrasound measurements comprising attenuation coefficient, backscatter coefficient, speed of sound, shear wave velocity, or shear wave viscosity and wherein converting comprises converting to the non-ultrasound biomarker of the other modality comprising a magnetic resonance-based, computed tomography-based, assay-based, or histology-based biomarker.

12. The method of claim 1 wherein converting comprises converting with the first conversion model comprising a function or a machine-learned model relating the one or more ultrasound measurements to the non-ultrasound biomarker.

13. The method of claim 1 wherein displaying comprises displaying the value for the non-ultrasound biomarker with an ultrasound image of the patient.

14. A method for an ultrasound-based proxy estimation with an ultrasound scanner, the method comprising:

receiving a user selection of a first conversion model for converting a plurality of ultrasound quantitative measurements to an estimate of MR-PDFF for a liver study of a patient, the plurality of ultrasound quantitative measurements comprising at least attenuation coefficient (AC) and backscatter coefficient (BSC);

defining a sequence of ultrasound transmissions to acquire ultrasound data based on the user selection of the first conversion model;

scanning, by the ultrasound scanner, the patient with the sequence of ultrasound transmissions;

estimating, by the ultrasound scanner, values for AC and BSC from the ultrasound data resulting from the scanning;

converting, using the first conversion model, the values for AC and BSC to an estimated value for MR-PDFF for the patient; and displaying the estimated value for MR-PDFF for the patient.

15. The method of claim 14 wherein scanning with the custom sequence comprises scanning with the ultrasound transmissions for the first and second ultrasound measurements being interleaved.

16. The method of claim 14 wherein scanning comprises scanning with the sequence being adaptive based on the plurality of quantitative ultrasound values.

17. The method of claim 14 wherein scanning comprises scanning with the sequence being adaptive based on the value for MR-PDFF.

18. A system for an ultrasound-based proxy estimation, the system comprising:

a user input configured to receive user entry of one or more models relating ultrasound parameters to one or more non-ultrasound parameters, the one or more models being in a list of multiple models for the one or more non-ultrasound parameters;

a transducer;

a beamformer configured to transmit and receive sequences of pulses in a patient with the transducer, the sequences of pulses selected from a plurality of sequences of pulse based on the selected one or more models in order to acquire the ultrasound parameters;

an image processor configured to generate a value for the one or more non-ultrasound parameters from values of the ultrasound parameters, wherein a value for a respective non-ultrasound parameter has a different unity and/or scale than values of the ultrasound parameters, wherein the values of the ultrasound parameters are estimated using the transmit and receive sequences of the pulses; and a display configured to display the score for an index of a disease activity based on the one or more non-ultrasound parameters.

19. The system of claim 18, wherein the one or more models relate ultrasound parameters to MR-PDFF, biopsy fibrosis, and NAS biomarkers for a liver study.

* * * * *